(12) United States Patent
Ichikawa et al.

(10) Patent No.: US 6,827,798 B1
(45) Date of Patent: Dec. 7, 2004

(54) CATHETER AND METHOD FOR MANUFACTURING THE SAME

(75) Inventors: Noriyuki Ichikawa, Fujinomiya (JP); Takafumi Sumino, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 564 days.

(21) Appl. No.: 09/717,236

(22) Filed: Nov. 22, 2000

(30) Foreign Application Priority Data

Nov. 26, 1999 (JP) .......................................... 11-336081

(51) Int. Cl.$^7$ .............................................. B32B 31/00
(52) U.S. Cl. .................... 156/73.1; 156/292; 156/308.2
(58) Field of Search ............... 156/73.1, 73.2, 156/290, 292, 308.2, 308.4, 580.1, 580.2, 583.1

(56) References Cited

U.S. PATENT DOCUMENTS

| | | |
|---|---|---|
| 4,554,034 A | 11/1985 | Ensminger |
| 4,955,895 A | 9/1990 | Sugiyama et al. |
| 5,176,637 A | 1/1993 | Sagae |
| 5,178,803 A | 1/1993 | Tsuchida et al. |
| 5,288,350 A | 2/1994 | Kita |
| 5,496,275 A | 3/1996 | Sirhan et al. |
| 5,759,191 A | 6/1998 | Barbere |

FOREIGN PATENT DOCUMENTS

| | | |
|---|---|---|
| EP | 0 992 260 | 4/2000 |
| JP | 10-118187 | 5/1998 |
| JP | 11-19213 | 1/1999 |

*Primary Examiner*—James Sells
(74) *Attorney, Agent, or Firm*—Burns, Doane, Swecker & Mathis, L.L.P.

(57) ABSTRACT

For manufacturing a catheter having an inner tube forming a first lumen and an outer tube arranged coaxially with the inner tube, a second lumen being formed between the inner tube and the outer tube, a mandrel is inserted for retaining the first lumen into the inner tube, and an ultrasonic horn is applied to the outer surface of the outer tube for oscillating ultrasonic waves, thereby fusion bonding the inner surface of the outer tube to the outer surface of the inner tube. The particular method permits easily bonding the inner tube and the outer tube to each other. Also, since thermal deformation is small, it is possible to manufacture a catheter, in which the obstacle to the inflow of the inflation fluid into the inflatable member is very small, and which exhibits a rapid response to inflation and deflation of the inflatable member.

4 Claims, 3 Drawing Sheets

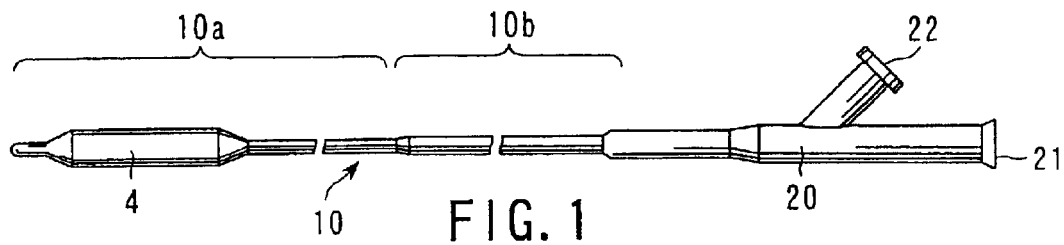
FIG. 1
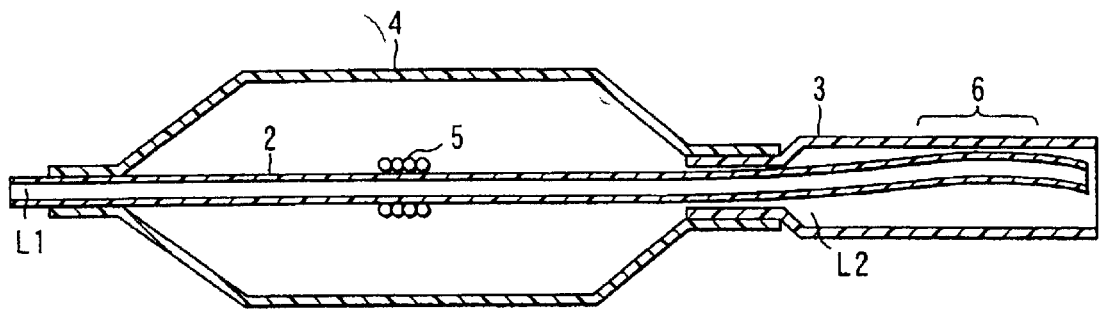
FIG. 2
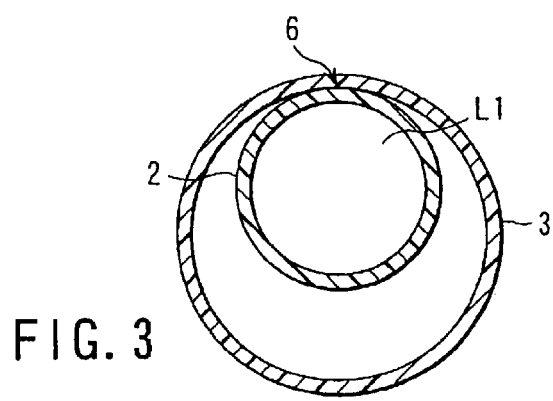
FIG. 3
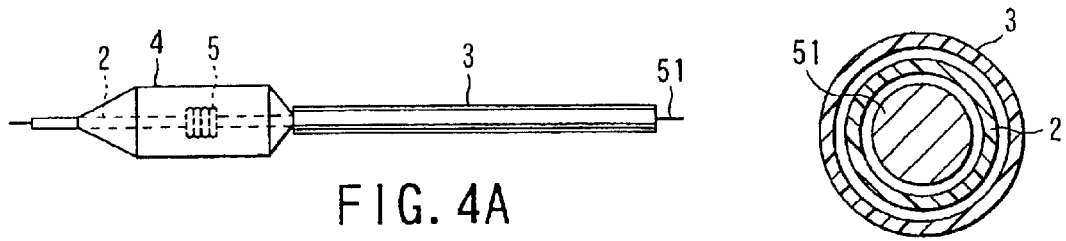
FIG. 4A
FIG. 4B

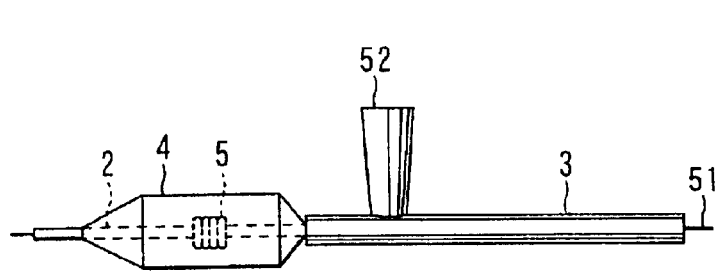 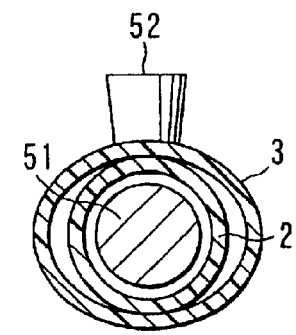
FIG. 5A  FIG. 5B
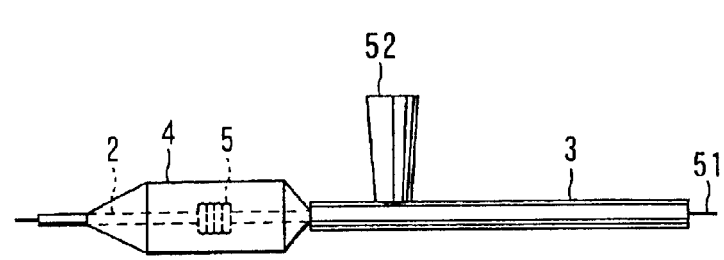 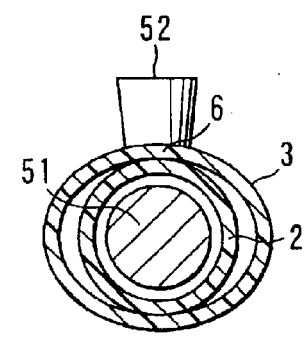
FIG. 6A  FIG. 6B
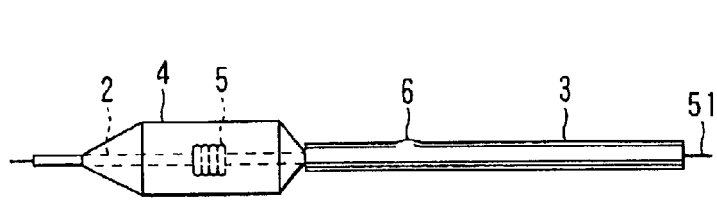 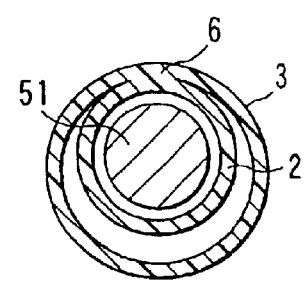
FIG. 7A  FIG. 7B

CATHETER AND METHOD FOR MANUFACTURING THE SAME

CROSS-REFERENCE TO RELATED APPLICATIONS

This application is based upon and claims the benefit of priority from the prior Japanese Patent Application No. 11-336081, filed Nov. 26, 1999, the entire contents of which are incorporated herein by reference.

BACKGROUND OF THE INVENTION

The present invention relates to a catheter such as a vasolidation catheter for dilating a stenosis within the blood vessel for curing the stenosis so as to improve the blood flow on the side of the periphery of the stenosis and a method for manufacturing the particular catheter.

The advent of a microcatheter has made it possible to perform therapy and diagnosis within a fine blood vessel or vasalium, though the conventional catheter is said to be incapable of performing such a therapy and diagnosis. The microcatheter includes, for example, a percutaneous transluminal coronary angioplasty catheter, hereinafter referred to as a PCTA dilatation catheter, used for curing the myocardial infarction or angina pectris. The PTCA dilatation catheter includes in general an outer tube having an inflation lumen, an inner tube having a guide wire lumen, an inflatable member (balloon) bonded in the vicinity of the distal ends of the inner tube and the outer tube, and a hub mounted to the proximal end portion of the inner tube and the outer tube. As described above, the catheter tube constituting the PTCA dilatation catheter requires at least two lumens. Therefore, a biaxial plastic tube, i.e., a plastic tube having openings in its cross section such as a double lumen, or a plastic tube of a coaxial structure such as a coaxial catheter tube is generally used for the PTCA dilatation catheter.

The PTCA dilation catheter formed of the biaxial catheter tube has an advantage that satisfactory pushability can be obtained. However, the biaxial catheter tube is poor in operability of the guide wire and is not suitable for decreasing the diameter of the catheter tube.

Under the circumstances, a catheter tube of a coaxial structure is mainly used in recent years for forming the PTCA dilatation catheter. The technology for improving trackability and pushability for the catheter of the coaxial structure within the blood vessel is disclosed in, for example, U.S. Pat. No. 5,496,275 and U.S. Pat. No. 5,759,191.

The catheter disclosed in U.S. Pat. No. 5,496,275 is constructed such that an inner tube and an outer tube are bonded to each other over a considerable distance between a position considerably away from a balloon toward the proximal end of the outer tube and the proximal end of the balloon so as to form a narrowed passageway for balloon inflation fluid. In this construction, it is necessary for the balloon inflation fluid to pass through a narrow fluid passageway from a position considerably in front of the balloon. Therefore, flow of the inflation fluid required for inflating the balloon is obstructed, resulting in a poor response time to inflation and deflation of the balloon.

The catheter discloses in U.S. Pat. No. 5,759,191 is constructed such that an inner tube and an outer tube are bonded to each other within a balloon with an annular spacer, and that a small opening is formed through the wall of the outer tube. In this construction, the balloon inflation fluid passes through the small opening made in the wall of the outer tube in a direction perpendicular to the long axis of the shaft so as to be injected into and discharged from the balloon. Therefore, the balloon inflation fluid fails to flow smoothly, resulting in a poor response time to inflation and deflation of the balloon. An additional problem is that, since the inner tube and the outer tube are bonded to each other, a troublesome manufacturing step is required.

Further, Japanese Patent Disclosure No. 11-19216 discloses a method of easily bonding an inner tube and an outer tube constituting a catheter tube. In this method, the inner tube and the outer tube are formed of compatible materials, and the outer tube is irradiated with a light beam for thermal fusion bonding of the tubes. In the method disclosed in this prior art, a mandrel for retaining a first lumen is inserted into the inner tube, and a mandrel for retaining a second lumen is inserted into the clearance between the inner tube and the outer tube. Under this condition, the outer tube is irradiated with the light beam. The reason that the mandrel for retaining the second lumen is inserted into the clearance between the inner tube and the outer tube is to prevent the second lumen from being blocked by thermal deformation of the inner and outer tubes caused by heat transfer to regions other than the focused region of the light beam. Since it is necessary to insert the mandrel for retaining the second lumen into the clearance between the inner and outer tubes, a troublesome manufacturing step is required in this prior art. In addition, since the outer tube is thermally deformed by the irradiation with the light beam not only on the inner surface but also on the outer surface, the appearance of the catheter is impaired.

BRIEF SUMMARY OF THE INVENTION

An object of the present invention is to provide a method for manufacturing a catheter, which permits easily bonding the inner tube and the outer tube to each other in a short time without using a mandrel for retaining a lumen between the inner tube and the outer tube.

Another object of the present invention is to provide a catheter being pushed favorably in the blood vessel, which is free from thermal deformation of the inner tube and the outer tube in regions other than the bonded portion, which is satisfactory in response time to inflation and deflation of the inflatable member because the interruption of the fluid passageway of the inflation fluid and the obstacle to the inflow of the inflation fluid into the inflatable member are negligibly small, and which is satisfactory in the appearance of the outer surface of the outer tube.

According to a first aspect of the present invention, there is provided a method for manufacturing a catheter comprising an inner tube forming a first lumen and an outer tube arranged coaxial with the inner tube, a second lumen being formed between the outer surface of the inner tube and the inner surface of the outer tube, comprising steps of: inserting a mandrel for retaining the first lumen into the inner tube; and applying an ultrasonic horn to the outer surface of the outer tube for oscillating ultrasonic waves, thereby fusion bonding the inner surface of the outer tube to the outer surface of the inner tube.

In the method of the present invention, the inner surface of the outer tube is fusion bonded to the outer surface of the inner tube by utilizing an ultrasonic oscillation. Therefore, the thermal deformation does not take place in portions other than the bonded portion. In addition, it is unnecessary to use a mandrel for retaining a second lumen between the inner tube and the outer tube during the bonding operation. Since it suffices to perform the fusion bonding operation utilizing an ultrasonic oscillation only with a mandrel for retaining the first lumen inserted into the inner tube as described above, the inner tube and the outer tube are bonded to each other easily and in a short time.

According to another aspect of the present invention, there is provided a catheter, comprising: an inner tube forming a first lumen and having an opening at a distal end; an outer tube arranged coaxially with the inner tube and having a distal end positioned at the proximal side to the distal end of the inner tube, a second lumen being formed between the outer surface of the inner tube and the inner surface of the outer tube; a deflated or folded inflatable member having a distal end portion secured to the inner tube and having a proximal end portion secured to the outer tube, and being in communication with the second lumen at the proximal end portion; a first port having an opening in communication with the first lumen; and a second port having an opening in communication with the second lumen; wherein a part of the inner surface of the outer tube is fusion bonded to a part of the outer surface of the inner tube by utilizing ultrasonic oscillation.

In the catheter of the present invention, only a region corresponding to at most 90% of the wall thickness of each of the outer tube and the inner tube from the bonding surface between the inner surface of the outer tube and the outer surface of the inner tube is thermally deformed. In other words, a region corresponding to at least 10% of the wall thickness of the outer tube from the outer surface of the outer tube and a region corresponding to at least 10% of the wall thickness of the inner tube from the inner surface of the inner tube are scarcely subjected to the thermal deformation. Also, those regions of the outer tube and the inner tube that are away from the bonded region are not subjected to the thermal deformation.

In the present invention, it is desirable for the bonded portion between the inner surface of the outer tube and the outer surface of the inner tube to be formed over a region corresponding to 5 to 95% of the outer circumferential surface of the inner tube and over a length of 0.3 to 30 mm in the axial direction.

In the catheter of the present invention, the inner tube and the outer tube are not thermally deformed in regions other than the bonded portion as described above. As a result, the interruption of the fluid passageway of the inflation fluid and the obstacle of the inflow of the inflation fluid into the inflatable member are very small, leading to a good response time to inflation and deflation of the inflatable member. In addition, appearance of the outer surface of the outer tube is kept favorable.

In the catheter of the present invention, the inner tube and the outer tube are fixed to each other at the bonded portion. Thus, the inner tube can be prevented from being bent, curved or twisted inside the outer tube. Therefore, a pushing force imparted to the proximal portion of the catheter is not absorbed by intermediate parts thereof but can be reliably transmitted to the distal end thereof. Thus, the pushability (trackability or travel performance in blood vessel) of the catheter in a blood vessel is preferable.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 shows the appearance of a catheter according to the present invention;

FIG. 2 is a cross sectional view showing the distal end section of the catheter shown in FIG. 1;

FIG. 3 is a cross sectional view showing the bonded portion of the inner tube and the outer tube in the catheter shown in FIG. 1;

FIG. 4A shows the appearance directed to the bonding method between the inner tube and the outer tube in the catheter of the present invention;

FIG. 4B is a cross sectional view of the catheter shown in FIG. 4A;

FIG. 5A shows the appearance directed to the bonding method between the inner tube and the outer tube in the catheter of the present invention;

FIG. 5B is a cross sectional view of the catheter shown in FIG. 5A;

FIG. 6A shows the appearance directed to the bonding method between the inner tube and the outer tube in the catheter of the present invention;

FIG. 6B is a cross sectional view of the catheter shown in FIG. 6A;

FIG. 7A shows the appearance directed to the bonding method between the inner tube and the outer tube in the catheter of the present invention;

FIG. 7B is a cross sectional view of the catheter shown in FIG. 7A;

DETAILED DESCRIPTION OF THE INVENTION

Figure 8:
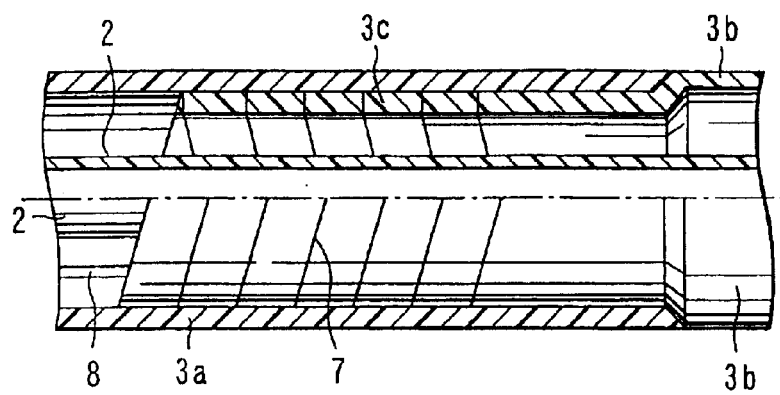
FIG. 8 is a cross sectional view showing the bonded portion between the outer tube on the side of the distal end and the outer tube on the side of the proximal end.

A catheter of the present invention and a method for manufacturing the catheter will now be described with reference to the accompanying drawings.

Specifically, FIG. 1 shows the appearance of a catheter according to one embodiment of the present invention. FIG. 2 is a cross sectional view showing the distal end section of the catheter shown in FIG. 1, and FIG. 3 is a cross sectional view showing the bonded portion between the inner tube and the outer tube in the catheter shown in FIG. 1. Further, FIGS. 4 to 7 show the appearances and the cross sectional views corresponding to respective steps of bonding the inner tube and the outer tube.

As shown in FIG. 1, a catheter 1 of the present invention comprises a catheter unit 10 and a branched hub 20 joined to the catheter unit 10. As described in detail herein later, the catheter unit 10 comprises an inner tube 2 forming a first lumen L1, an outer tube 3 arranged outside the inner tube 2 to form a second lumen L2 with the inner tube 2, and an inflatable member (balloon) 4. Also, the catheter unit 10 can be classified into a distal end section 10a and a main section 10b. The branched hub 20 includes a first port (guide wire port) 21 having an opening in communication with the first lumen L1 and a second port (injection port) 22 having an opening in communication with the second lumen L2.

The distal end section 10a of the catheter unit 10 is described with reference to FIG. 2. The inner tube 2 forms the first lumen L1, and the first lumen L1 is open at the distal end of the catheter unit 10. The outer tube 3 is arranged coaxially with the inner tube 2 and also is arranged such that the distal end of the outer tube 3 is positioned at the proximal side to the distal end of the inner tube 2. The second lumen L2 having a sufficiently large volume is formed between the inner surface of the outer tube 3 and the outer surface of the inner tube 2.

The inflatable member (balloon) 4 is secured to the distal end portion of the inner tube 2 in its distal end portion and is secured to the distal end portion of the outer tube 3 in its proximal end portion with an adhesive agent or fused thereto. The inner space of the inflatable member 4 is in communication with the second lumen L2 at its proximal end portion. When the inflatable member 4 is not inflated, the inflatable member 4 is deflated or folded on the outer circumferential surface of the inner tube 2. When the inflatable member 4 is inflated, at least a part of the inflatable member 4 is made cylindrical (or forms a column having a polygonal cross section), making it possible to dilate easily the stenosis of the blood vessel. A marker 5 made of a material having a high capability of forming an X-ray image is formed on the outer surface of the inner tube 2 in a position corresponding to the central portion in the cylindrical portion of the inflatable member 4. Incidentally, it is possible to form a second marker (not shown) on the outer surface of the inner tube 2 in a position corresponding to the proximal end portion of the cylindrical portion of the inflatable member 4. Further, it is also possible to form two markers on the outer surface of the inner tube 2 in positions corresponding to the both ends of the cylindrical portion of the inflatable member 4.

The outer surface of the inner tube 2 and the inner surface of the outer tube 3 are fusion bonded to each other in a position rearward of the proximal end of the inflatable member 4 so as to form a bonded portion 6. Because of fixing the inner tube 2 to the outer tube 3 at the bonded portion 6, the inner tube 2 can be prevented from being bent, curved or twisted inside the outer tube 3. Therefore, a pushing force imparted to the proximal portion of the catheter 1 is not absorbed by intermediate parts thereof but can be reliably transmitted to the distal end thereof. Thus, the pushability (trackability or travel performance in blood vessel) of the catheter 1 in a blood vessel is preferable. Since the bonded portion 6 shown in FIG. 2 is formed rearward of the proximal end portion of the inflatable member 4, the flexibility is not impaired in the portion of the inflatable member 4, making it possible to provide a catheter excellent in pushability into the blood vessel and in trackability. Alternatively, it is also possible to allow the outer tube 3 to extend into the inflatable member 4 so as to be bonded to the inner tube 2 in a position forward of the proximal end of the inflatable member 4. FIG. 3 is a cross sectional view showing the outer tube 3 and the inner tube 2 at the position of the bonded portion 6.

How to bond the outer tube 3 and the inner tube 2 will now be described with reference to FIGS. 4A to 7B. Each of FIGS. 4A, 5A, 6A and 7A shows the appearance of the distal end section of the catheter. Also, each of FIGS. 4B, 5B, 6B and 7B is a cross sectional view at the position of the bonded portion.

As shown in FIGS. 4A and 4B, a mandrel 51 for retaining the first lumen L1 is inserted into the inner tube 2. It is desirable for the outer diameter of the mandrel 51 to be equal to the inner diameter of the inner tube or smaller by about 0.1 mm than the inner diameter of the inner tube 2. In the present invention, it is unnecessary to use in this step a second mandrel for retaining a second lumen as disclosed in Japanese Patent Disclosure No. 11-19216 referred to previously.

In the next step, as shown in FIGS. 5A and 5B, an ultrasonic horn 52 is applied to the outer surface of the outer tube 3 in a position rearward of the proximal end of the inflatable member 4 with a predetermined pressure, preferably with 50 to 5000 gf. Then, as shown in FIGS. 6A and 6B, ultrasonic waves are oscillated from the ultrasonic horn 52 so as to achieve a fusion bonding between the inner surface of the outer tube 3 and the outer surface of the inner tube 2. In this fashion, the bonded portion 6 is formed as shown in FIGS. 7A and 7B. By fixing the outer surface of the inner tube 2 to the inner surface of the outer tube 3 by fusion bonding as described above, it is possible to ensure a sufficient pushability of the catheter into the blood vessel and a sufficient trackability within the blood vessel.

In the ultrasonic bonding employed in the present invention, utilized is the inner heat generation at the contact surface between the inner surface of the outer tube 3 and the outer surface of the inner tube 2. As a result, it is possible to selectively heat only that region which is to be bonded, and the heat is unlikely to be transmitted to other regions. It follows that the thermal deformation takes place in only a region corresponding to at most 90% of the wall thickness of each of the outer tube 3 and the inner tube 2 from the bonded surface in the bonded portion 6. In other words, the thermal deformation is scarcely brought about in a region corresponding to at least 10% of the wall thickness of the outer tube 3 from the outer surface of the outer tube 3 and in a region corresponding to at least 10% of the wall thickness of the inner tube 2 from the inner surface of the inner tube 2. Further, the outer tube 3 and the inner tube 2 are not thermally deformed in regions apart from the bonded portion 6.

What should be noted is that, in the present invention, the lumen is neither blocked nor narrowed, though the conventional technique of inserting a mandrel for retaining a lumen between the outer tube and the inner tube is not employed. As a result, the cross sectional area of the second lumen L2 in the bonded portion is substantially equal to the cross sectional area of the second lumen L2 in regions other than the bonded portion. It follows that the fluid flow into and out of the inflatable member 4 through the second lumen L2 are carried out satisfactorily. In addition, the appearance of the outer tube 3 is not impaired. Also, since the thermal deformation is small as described above, the conventional technique of using a mandrel for retaining the second lumen need not be employed in the present invention. It follows that the outer tube 3 and the inner tube 2 can be bonded to each other in a very short time.

It is desirable for the bonded portion 6 between the inner surface of the outer tube 3 and the outer surface of the inner tube 2 in 5 to 95% of the circumferential outer surface of the inner tube 2 and over a length of 0.3 to 30 mm in the axial direction.

The construction of that portion of the catheter positioned closer to the proximal end than the portion shown in FIG. 2 will now be described.

As shown in FIG. 8, the outer tube 3 comprises a distal end side outer tube 3a and a main section side outer tube 3b bonded to each other. The distal end portion of the main section side outer tube 3b constitutes an insertion portion 3c having an outer diameter substantially equal to the inner diameter of the distal end side outer tube 3a. The insertion portion 3c is inserted into the proximal end portion of the distal end side outer tube 3a. Further, as shown in FIG. 1, the distal end side outer tube 3a is tapered into a small diameter on the side of the distal end relative to the bonded portion with the main section side outer tube 3b. A slit 7 is formed spirally in the insertion portion 3c of the main section side outer tube 3b. The slit 7 extends from the distal end or a position slightly rearward of the distal end of the insertion portion 3c to reach a position slightly forward of the proximal end of the insertion portion 3c. A region in which the slit 7 is not formed is included in the proximal end portion of the insertion portion 3c. The distal end side outer tube 3a and the main section side outer tube 3b are fixed in the region in which the slit 7 is not formed, and the distal end side outer tube 3a and the main section side outer tube 3b are not fixed in the slit-forming region. If the particular slit 7 is formed, the bonded portion is made flexible so as to permit the distal end portion of the main section side outer tube 3b to be bent more naturally. As a result, the operability of the catheter is more improved. Incidentally, it is possible to form a large number of fine holes in place of the slit 7.

Figure 9:
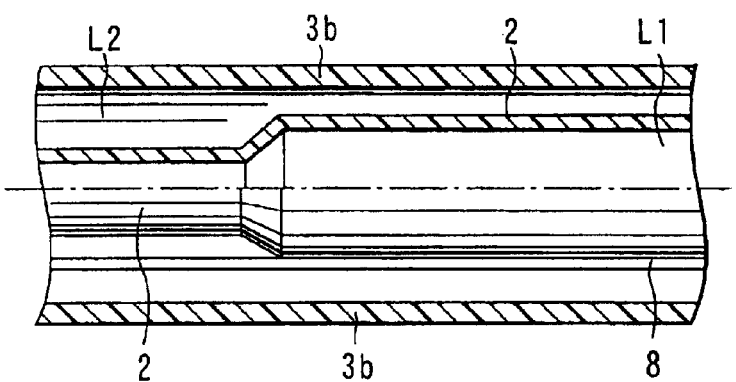
FIG. 9 is a cross sectional view showing a tapered portion of the inner tube.

As show in FIG. 9, the inner tube 2 comprises a tapered portion in a position slightly rearward of the bonded portion between the distal end side outer tube 3a and the main selection side outer tube 3b. The distal end portion of the inner tube 2 relative to the tapered portion has a small diameter and the portion on the side of the main section has a diameter larger than that on the side of the distal end.

Figure 10:
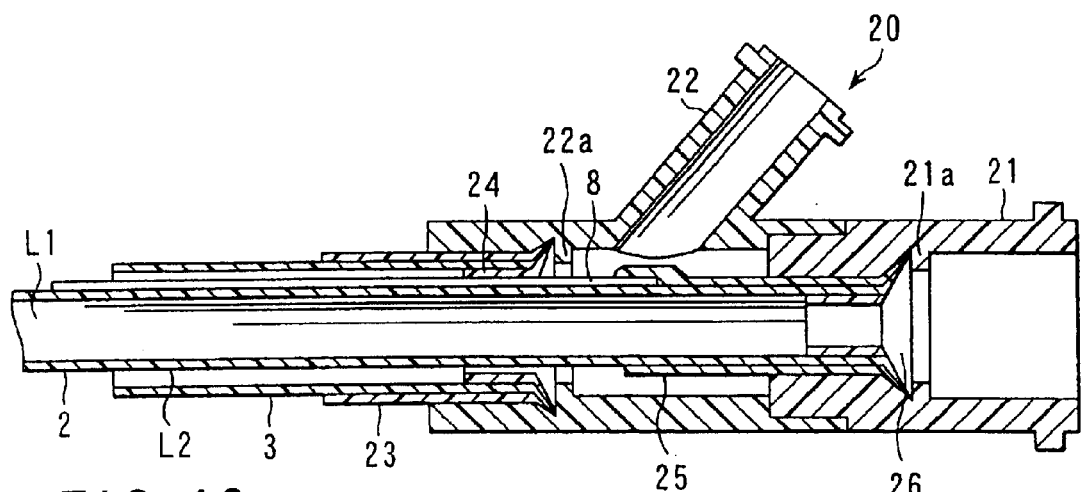
FIG. 10 is a cross sectional view showing the proximal end portion of the catheter of the present invention.

The proximal end portion of the catheter 1 of the present invention is shown in detail in FIG. 10. A branched hub 20 is fixed to the proximal end portion of the catheter unit 10. The branched hub 20 includes the first port (guide wire port) 21 having an opening in communication with the first lumen L1 and the second port (injection port) 22 having an opening in communication with the second lumen L2.

The proximal end portion of the outer tube 3 is covered with a tube 23 for preventing the bending. The bending preventing tube 23 is formed by covering the proximal end portion of the outer tube 3 with a tube of a thermally shrinkable resin having an inner diameter slightly smaller than the outer diameter of the outer tube 3 after the thermal shrinkage, followed by blowing a hot air against the thermally shrinkable tube so as to heat and thermally shrink the tube. The bending preventing tube 23 is fixed by pushing a stopper pin 24 into a projection 22a formed in the inner surface of the second port 22. To be more specific, the stopper pin 24 having an enlarged proximal end portion is inserted into the proximal end of the outer tube 3, and the proximal end of the outer tube 3 is inserted into the distal end portion of the second port 22 until the proximal end portion of the stopper pin 24 is pushed over the projection 22a so as to fix the bending preventing tube 23. In this case, it is possible to coat the contact surface between the second port 22 and the bending preventing tube 23 with an adhesive so as to fix the bending preventing tube 23.

Likewise, the proximal end portion of the inner tube 2 is covered with a tube 25 for preventing the bending. The bending preventing tube 25 is formed by covering the proximal end portion of the inner tube 2 with a tube of a thermally shrinkable resin having an inner diameter slightly smaller than the outer diameter of the inner tube 2 after the thermal shrinkage, followed by blowing a hot air against the thermally shrinkable tube so as to heat and thermally shrink the tube. The bending preventing tube 25 is fixed by pushing a stopper pin 26 into a projection 21a formed in the inner surface of the first port 21. To be more specific, the stopper pin 26 having an enlarged proximal end portion is inserted into the proximal end of the inner tube 2, and the proximal end of the inner tube 2 is inserted into the distal end portion of the first port 21 until the proximal end portion of the stopper pin 26 is pushed over the projection 21a so as to fix the bending preventing tube 25. In this case, it is possible to coat the contact surface between the first port 21 and the bending preventing tube 25 with an adhesive so as to fix the bending preventing tube 25.

Also, the distal end portion of the first port 21 is inserted into the proximal end of the second port 22 so as to permit the first port 21 and the second port 22 to be engaged with each other. In this case, the contact surface between the first port 21 and the second port 22 is coated with an adhesive so as to permit the first port 21 and the second port 22 to be fixed to each other without fail.

Incidentally, the construction of the proximal end portion of the catheter 1 of the present invention is not limited to the construction shown in FIG. 10. For example, it is possible to mount in a fluid-tight fashion a tube having a port member to each of the proximal end of the inner tube 2 and the proximal end of the outer tube 3 in place of mounting the branched hub 20.

As shown in FIGS. 8 to 10, a rigidity imparting body 8 made of a metal wire is inserted into the second lumen L2 defined between the inner tube 2 and the outer tube 3 over a region ranging between the proximal end portion of the branched hub 20 and the distal end section 10a of the catheter unit 10. The rigidity imparting body 8 is intended to prevent the catheter unit 10 from being bent excessively in the bent portion without unduly lowering the flexibility of the catheter and is also intended to facilitate the pushing of the distal end section of the catheter.

The proximal end portion of the rigidity imparting body 8 is fixed to the outer surface of the proximal end portion of the inner tube 2 by the bending preventing tube 25 covering the proximal end portion of the inner tube 2. Incidentally, it is possible to fix the proximal end portion of the rigidity imparting body 8 to the inner surface of the proximal end portion of the outer tube 3. It should be noted that the rigidity imparting body 8 is not fixed in portions other than the proximal end portion.

Figure 11:
FIG. 11 shows the small diameter portion of a rigidity imparting body.

As shown in FIG. 11, the distal end portion of the rigidity imparting body 8 is made thinner than the other portion. The distal end portion is processed by the method of, for example, polishing. As shown in FIG. 8, the distal end of the thin portion of the rigidity imparting body 8 extends to reach a region in the vicinity of the distal end portion of the main section side outer tube 3a. It is possible for the distal end of the thin portion of the rigidity imparting body 8 to extend to reach a region in the vicinity of the distal end of the distal end side outer tube 3a.

As described above, the rigidity imparting body 8 is not fixed in the region other than the proximal end portion and, thus, can be moved relatively freely within the second lumen L2. If the rigidity imparting body 8 is movable within the second lumen L2, it is possible to prevent the catheter unit 10 from winding within the blood vessel. As a result, the pushing force imparted to the proximal end of the catheter unit 10 is prevented from being absorbed in the winding portion, which makes it possible to transmit the pushing force to the distal end of the catheter without fail. It follows that the operability of the catheter can be improved. In particular, it is possible to facilitate the pushing operation of the distal end section of the catheter, in which the inflatable member 4 is bonded, into the stenosis of the blood vessel. It is also possible to insert the distal end section of the catheter into the marked stenosis within the blood vessel (sub-complete obturation).

In order to obtain a good operability described above, it is desirable for the proximal end portion of the rigidity imparting body 8 to be more rigid than the distal end portion. If the cross sectional area of the proximal end portion of the rigidity imparting body 8 is larger than that of the distal end portion, the proximal end portion is made more rigid than the distal end portion. Also, a higher flexibility and a higher rigidity can be imparted to the distal end portion and the main portion, respectively, of the rigidity imparting body 8 by bringing about a temperature gradient in the annealing after the cold working of the metal wire used as the rigidity imparting body 8 such that the temperature is made higher on the distal end side and lower on the main portion side. It is also possible to use a stranded wire prepared by stranding a plurality of thin wires as the rigidity imparting body 8.

The materials, sizes, etc., of the constituents of the catheter of the present invention will now be described.

The inner tube 2 is formed of a material that is flexible to some extent including, for example, polymer materials such as polyolefin (e.g., polyethylene, polypropylene, polybutene, ethylene-propylene copolymer, ethylene-vinyl acetate copolymer, ionomer and a mixture of at least two kinds of them), cross-linked polyolefin, polyvinyl chloride, polyamide, polyamide elastomer, polyester, polyester elastomer, polyurethane, polyurethane elastomer, polyimide, fluoroplastic, and a mixture thereof.

The inner tube 2 has a length of 300–2000 mm, more preferably 300–1500 mm, and a wall thickness of 10–150 $\mu$m, more preferably 20–100 $\mu$m. The outer diameter of the inner tube 2 is designed to −0.30–2.00 mm, preferably 0.40–1.80 mm, on the distal end side, and to 0.40–2.50 mm, preferably 0.55–2.40 mm, on the main section side. Further, the outer diameter of the inner tube 2 may be designed to 0.1–1.0 mm, preferably 0.3–0.7 mm, at the most distal end.

The inner tube having different diameters as above can be prepared by any method, for example, by individually forming the inner tubes of the distal end the side and the proximal end side, respectively, followed by bonding them, by applying a secondary processing such as pull-down, or by making the diameter on the distal end side smaller than that on the proximal end side by extrusion.

The material of the outer tube should be capable of ultrasonic bonding with the inner tube and should be flexible to some extent. The materials for the outer tube include, for example, polymer materials such as polyolefin (e.g., polyethylene, polypropylene, polybutene, ethylene-propylene copolymer, ethylene-vinyl acetate copolymer, ionomer and a mixture of at least two kinds of them), cross-linked polyolefin, polyvinyl chloride, polyamide, polyamide elastomer, polyester, polyester elastomer, polyurethane, polyurethane elastomer, fluoroplastic, polyimide and a mixture thereof. It is desirable for the material of the outer tube to be equal to the material of the inner tube.

Where the outer tube 3 is prepared by bonding the distal end side outer tube 3a and the main section side outer tube 3b, it is possible for these tubes to be made of different materials. For example, it is desirable to use a material having a high rigidity such as a polyimide-based resin for forming the main section side outer tube 3b, and to use a material having flexibility, compared with the material of the tube 3b, such as a polyamide-based resin for forming the distal end side outer tube 3a.

The outer tube 3 has a length of 300–2000 mm, preferably 300–1500 mm, and a wall thickness of 25–200 $\mu$m, preferably 50–100 $\mu$m. The outer diameter of the outer tube 3 is designed to 0.50–1.5 mm, preferably 0.60–1.1 mm, in the small diameter portion of the distal end side outer tube 3a, and to 0.75–1.5 mm, preferably 0.9–1.1 mm in the proximal end portion of the distal end side outer tube 3a and in the main section side outer tube 3a.

It is desirable for the inflatable member 4 to be made of a material capable of dilating the stenosis of the blood vessel and having flexibility to some extent. The materials for the inflatable member 4 include, for example, polyolefin (e.g., polyethylene, polypropylene, polybutene, ethylene-propylene copolymer, ethylene-vinyl acetate copolymer, ionomer and a mixture of at least two kinds of them), cross-linked polyolefin, polyester such as polyethylene terephthalate, polyester elastomer, polyvinyl chloride, polyurethane, polyurethane elastomer, polyphenylene sulfide, polyamide, polyamide elastomer, fluoroplastic, silicone rubber and a latex rubber. It is also possible to use a laminated film prepared by suitably laminating these materials.

The outer diameter of the cylindrical portion of the inflatable member 4 when inflated is 1.0–10 mm, preferably 1.0–5.0 mm. The length of the cylindrical portion of the inflatable member 4 is 5–50 mm, preferably 10–40 mm. Further, the entire length of the inflatable member 4 is 10–70 mm, preferably 15–60 mm.

It is desirable for the marker 5 to be made of a material having a high capability of forming an X-ray image including, for example, Pt, Pt alloy, W, w alloy, Au, Au alloy, Ir, Ir alloy, Ag and Ag alloy. It is desirable for the marker 5 to be formed in the shape of a coil spring or a ring.

It is desirable for the branched hub 20 including the first port 21 and the second port 22 to be made of a thermoplastic resin such as polycarbonate, polyamide, polysulfone, polyarylate, or methacrylate-butylene-styrene terpolymer.

It is desirable for the rigidity imparting body 8 to be made of an elastic metal such as stainless steel or a superelastic alloy. In particular, it is desirable to use a high tensile stainless steel, which is generally used for manufacturing a spring, and a Ni/Ti alloy wire, which has superelasticity for forming the rigidity imparting body 8.

The diameter of the rigidity imparting body 8 is designed to 0.05–1.5 mm, preferably 0.10–1.0 mm. Where the diameter of the rigidity imparting body 8 is made smaller on the distal end side, it is desirable for the outer diameter of the small diameter portion to be about $\frac{1}{5}$ to $\frac{1}{10}$ the outer diameter on the proximal end side.

The catheter of the present invention is not limited to a so-called over-the-wire type described above. It is also possible for the catheter of the present invention to be of a so-called rapid exchange type, in which the first port is disposed on the distal end side relatively to the hub. Also, it is desirable to apply a treatment to impart lubricating properties to the outer surfaces of the outer tube 3 and the inflatable member 4 in order to facilitate the insertion of the catheter 1 into a blood vessel or into a guide catheter. The lubricating treatment can be applied by means of coating of a hydrophilic polymer such as poly(2-hydroxyethyl methacrylate), polyhydroxyethyl acrylate, hydroxypropyl cellulose, methyl vinyl ether-maleic anhydride copolymer, polyethylene glycol, polyacrylamide or polyvinyl pyrrolidone, or by means of coating or fixation of a material satisfactory in lubricity such as a reactive silicone resin having polydimethyl siloxane on the main chain.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for manufacturing a catheter comprising an inner tube forming a first lumen and an outer tube arranged coaxially with the inner tube, a second lumen being formed between the outer surface of the inner tube and the inner surface of the outer tube, comprising steps of:

inserting a mandrel for retaining the first lumen into the inner tube; and applying ultrasonic waves to utilize heat generation at a contact surface between the inner surface of the outer tube and the outer surface of the inner tube thereby fusion bonding the inner surface of the outer tube to the outer surface of the inner tube.

2. The method according to claim 1, wherein each of the inner tube and the outer tube is made of a polymer material.

3. The method according to claim 2, wherein each of the inner tube and the outer tube is made of the same polymer material.

4. The method according to claim 1, wherein the ultrasonic waves are applied without mandrel being positioned between the inner surface of the outer tube and the outer surface of the inner tube.

* * * * *